United States Patent
Price et al.

(10) Patent No.: US 8,177,713 B2
(45) Date of Patent: May 15, 2012

(54) MOTOR-DRIVEN LAPAROSCOPIC SEAL ASSEMBLY

(75) Inventors: Daniel W. Price, Loveland, OH (US); Gregory W. Johnson, Milford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1190 days.

(21) Appl. No.: 11/798,633

(22) Filed: May 15, 2007

(65) Prior Publication Data

US 2008/0284114 A1    Nov. 20, 2008

(51) Int. Cl.
*A61B 1/32* (2006.01)
(52) U.S. Cl. .................................................... 600/206
(58) Field of Classification Search .......... 600/201–210, 600/104, 117, 121, 123–125; 606/108; 277/626, 277/627; 604/167.01–167.03, 167.06
See application file for complete search history.

(56) References Cited

U.S. PATENT DOCUMENTS

| | | | |
|---|---|---|---|
| 4,094,492 A | 6/1978 | Beeman et al. | |
| 7,393,322 B2 | 7/2008 | Wenchell | |
| 2005/0222582 A1* | 10/2005 | Wenchell | 606/108 |
| 2008/0058604 A1* | 3/2008 | Sorensen | 600/208 |
| 2008/0146884 A1 | 6/2008 | Beckman et al. | |

* cited by examiner

*Primary Examiner* — Eduardo C Robert
*Assistant Examiner* — Tara Carter
(74) *Attorney, Agent, or Firm* — Welsh Flaxman & Gitler LLC

(57) ABSTRACT

A motor driven seal assembly for permitting hand assisted laparoscopic procedures. The seal assembly includes a seal cap having a seal positioned within a housing, the housing includes a lower seal ring having a track which supports an upper seal ring for rotational motion relative thereto. The seal is supported between the upper seal ring and the lower seal ring for rotation between an open orientation and a closed orientation. A motor-driven drive assembly is associated with the lower seal ring and the upper seal ring for controlling relative to movement thereof.

16 Claims, 8 Drawing Sheets

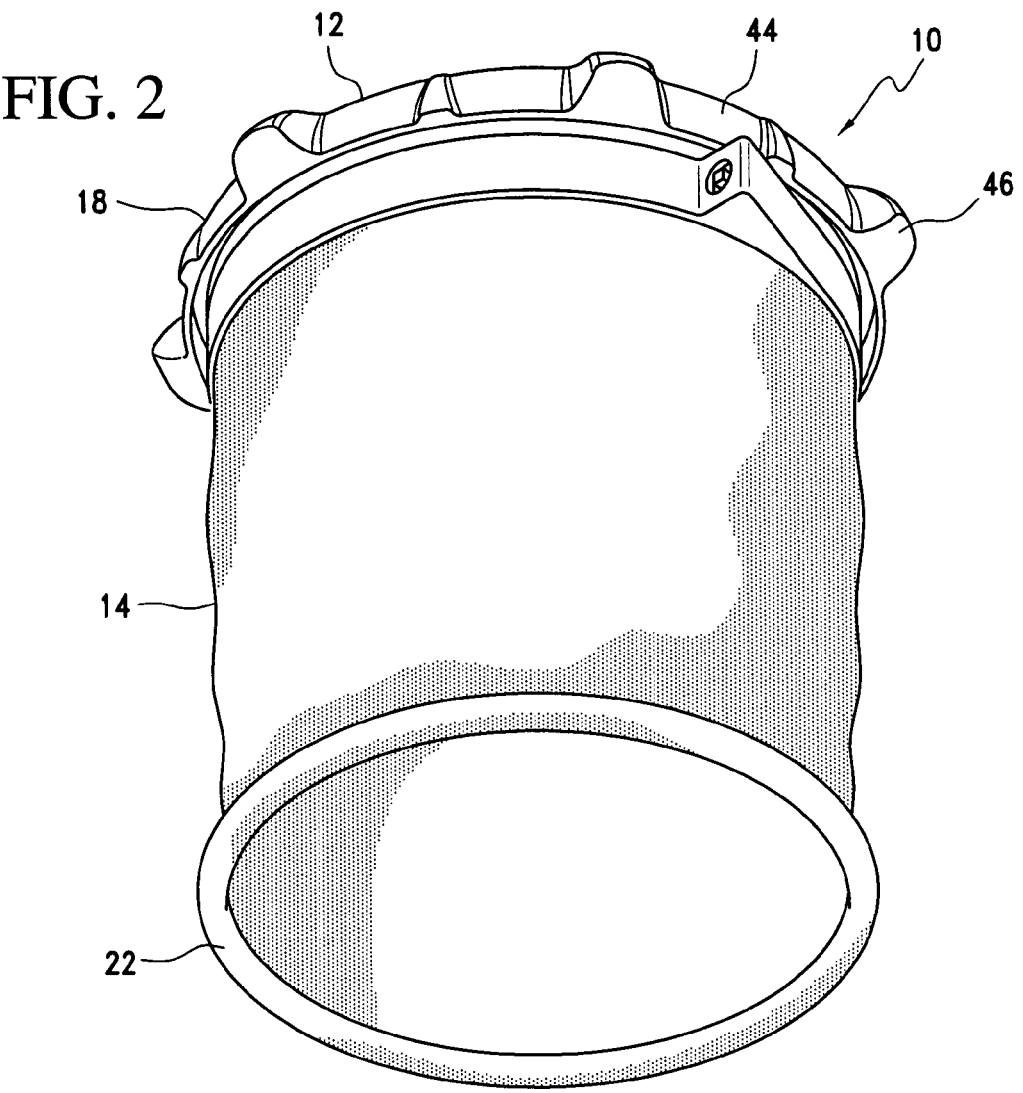
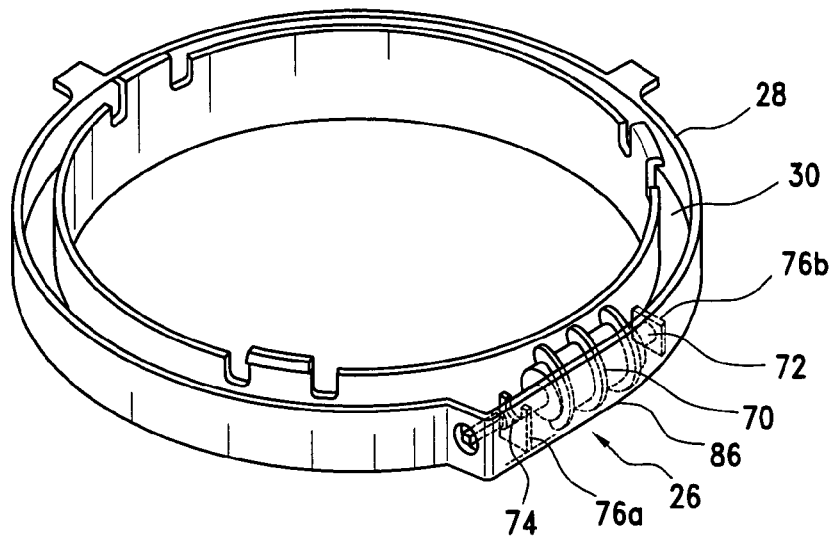

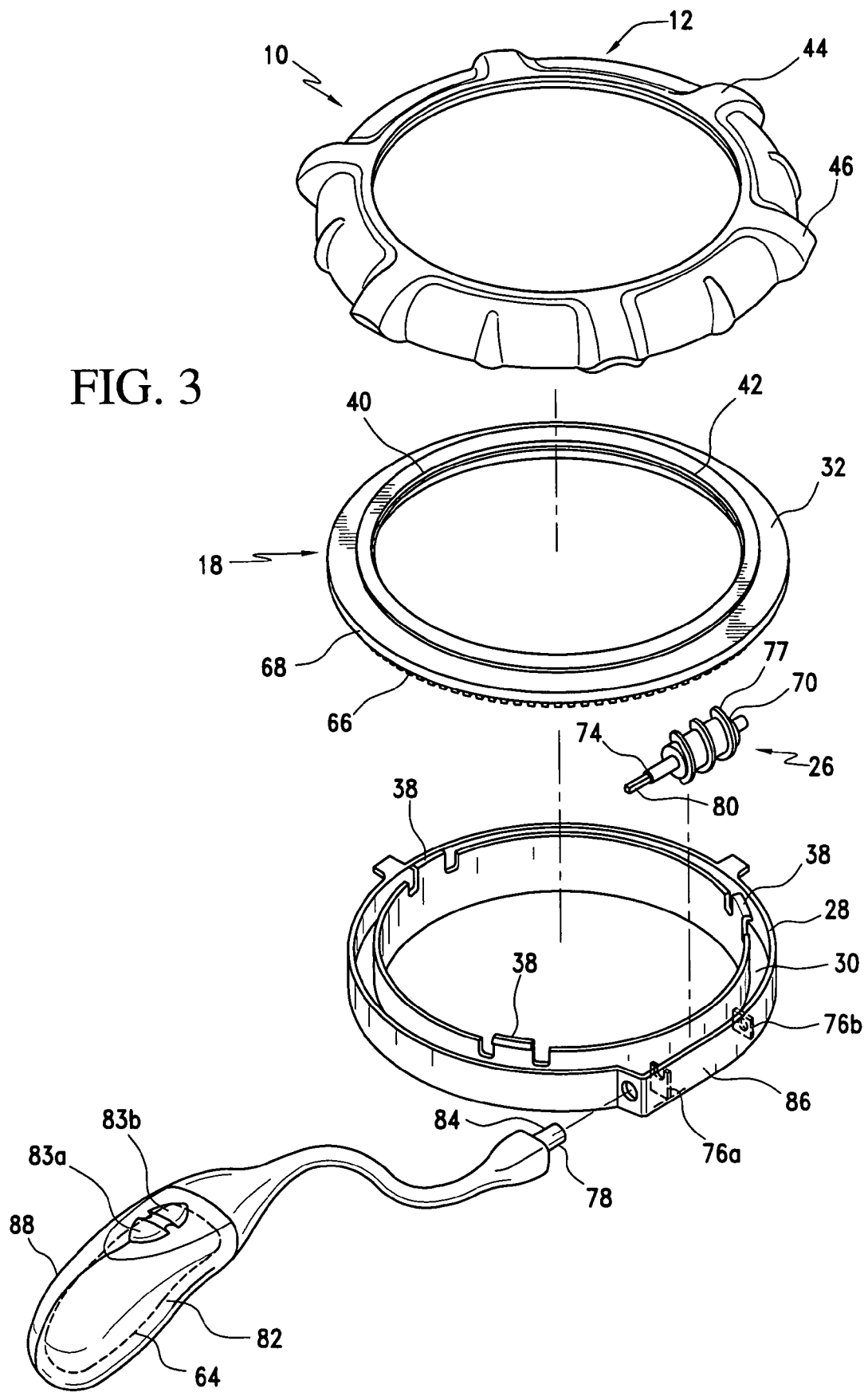

MOTOR-DRIVEN LAPAROSCOPIC SEAL ASSEMBLY

BACKGROUND OF THE INVENTION

1. Field of the Invention

The invention relates to laparoscopic devices. In particular, the invention relates to a motor-driven laparoscopic seal assembly providing for controlled opening and closing of the seal.

2. Description of the Related Art

During laparoscopic procedures, it is often desirable for the surgeon to place his or her hand within the patient in a manner manipulating the instruments positioned within the patient. When this occurs, it is desirable to separate the external environment from the internal portion of the patient. For example, when hand assisted laparoscopic procedures are performed within the abdominal cavity, it is desirable to perform hand exchanges with minimal loss of abdominal pressure. As such, a need exists for skin mountable seals permitting hand assisted laparoscopic procedures without fear that the abdominal pressure will be compromised. The present invention provides such an apparatus.

SUMMARY OF THE INVENTION

It is, therefore, an object of the present invention to provide a seal assembly for permitting hand assisted laparoscopic procedures. The seal assembly includes a seal cap having a seal positioned within a housing, the housing including a lower seal ring having a track which supports an upper seal ring for rotational motion relative thereto. The seal is supported between the upper seal ring and the lower seal ring for rotation between an open orientation and a closed orientation. A motor-driven drive assembly is associated with the lower seal ring and the upper seal ring for controlling relative to movement thereof.

It is also an object of the present invention to provide a seal assembly including a retractor extending from the seal cap.

It is another object of the present invention to provide a seal assembly wherein the drive assembly includes a worm gear.

It is also a further object of the present invention to provide a seal assembly wherein the worm gear engages teeth formed along the upper seal ring.

It is still a further object of the present invention to provide a seal assembly wherein the drive assembly includes a pinion gear.

It is yet a further object of the present invention to provide a seal assembly wherein the pinion gear engages a belt encircling the upper seal ring.

It is also an object of the present invention to provide a seal assembly wherein the pinion gear engages teeth formed along the upper seal ring.

It is another object of the present invention to provide a seal assembly wherein the seal in an iris seal.

It is still a further object of the present invention to provide a seal assembly including a hand-held motor assembly adapted for use in conjunction with the motor-driven drive assembly.

It is also an object of the present invention to provide a seal assembly wherein the hand-held motor assembly includes a drive cable.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 2 is a bottom perspective view of the seal assembly shown in FIG. 1.

FIG. 3 is an exploded view of the seal assembly.

FIG. 4 is a perspective view of the lower seal ring of the seal assembly shown with reference to FIG. 1.

DESCRIPTION OF THE PREFERRED EMBODIMENTS

Figure 1:
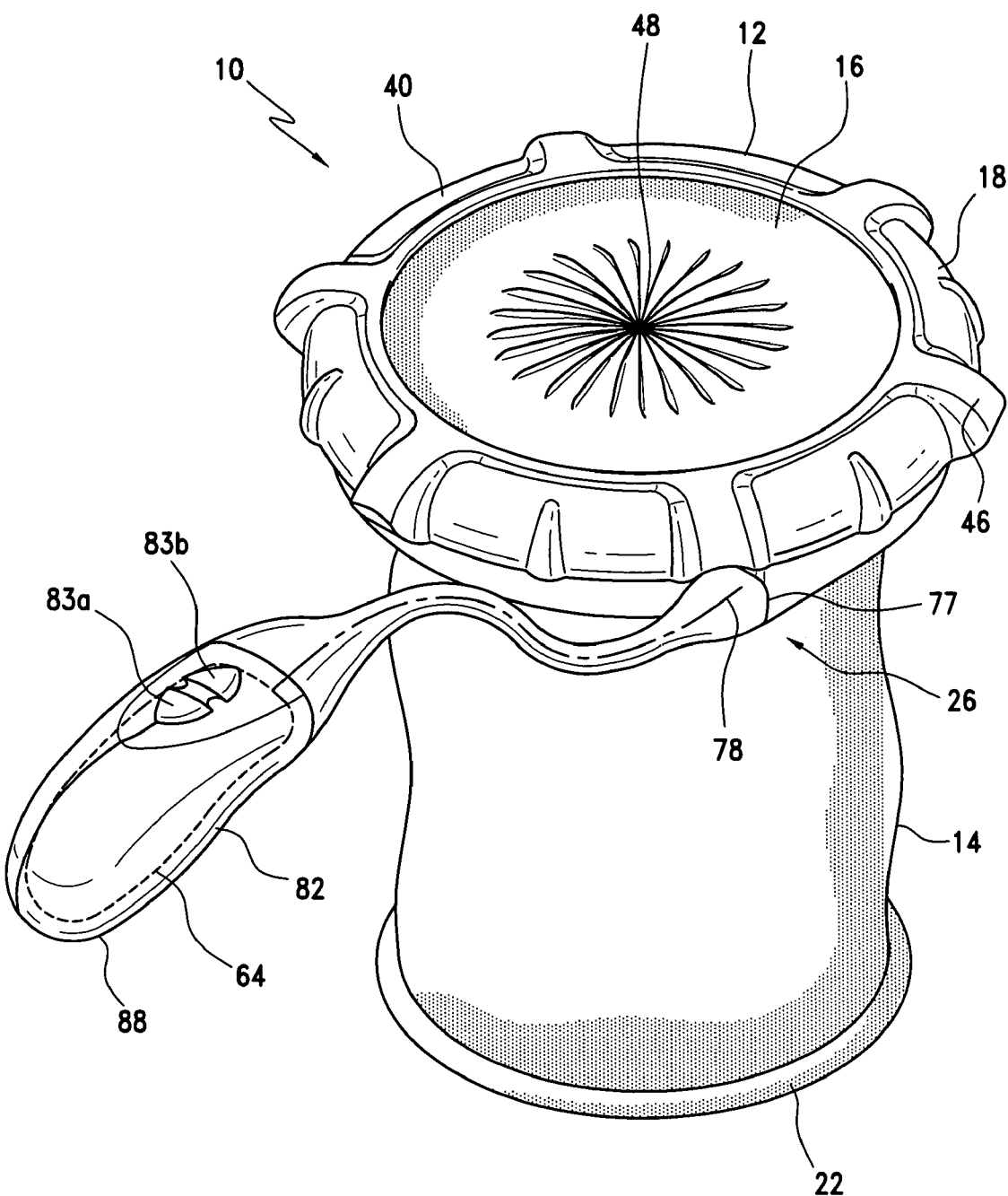
FIG. 1 is a perspective view of a laparoscopic seal assembly in accordance with the preferred embodiment of the present invention.
Figure 5:
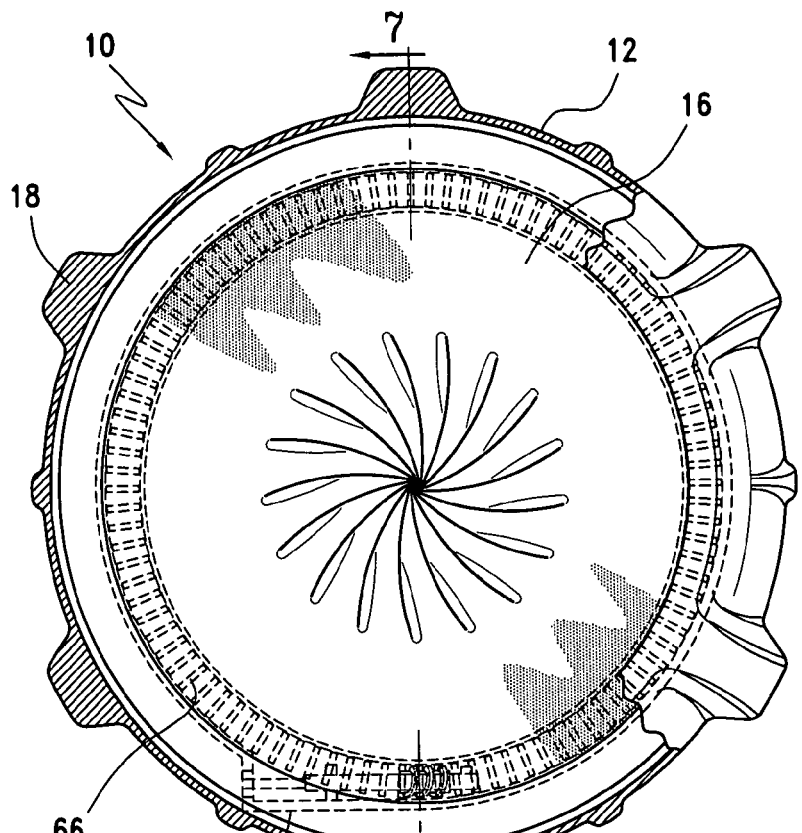
FIGS. 5 and 6 are partial sectional top views showing actuation of the present hand assisted laparoscopic seal assembly respectively between a closed and an open orientation.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

Referring to FIGS. 1 to 8, a seal assembly 10 for permitting hand assisted laparoscopic procedures is disclosed. The seal assembly 10 generally employs an iris seal cap 12 and retractor 14 to ensure abdominal pressure is not compromised during hand exchanges while hand assisted laparoscopic procedures are performed. In accordance with a preferred embodiment of the present invention, the seal assembly 10 includes an iris seal 16 housed within the seal cap 12. The iris seal 16, in conjunction with the motor-driven drive assembly 26, creates a gas tight barrier around the surgeon's wrist or instrument when inserted through the seal assembly 10 and also creates a gas tight barrier between the interior abdominal space and the external environment when a hand is not inserted through the seal assembly 10. As will be discussed below in greater detail, adjustment of the iris seal 16, and ultimately the access opening 48, provides for access to a body cavity in a highly controlled manner.

Referring to the various figures, the seal cap 12 includes an iris seal 16 positioned within a housing 18. The housing 18 is made of soft textured material such as the thermoplastic elastomer SANTOPRENE, or other like materials, and supports the iris seal 16 in a concentric manner. Although SANTOPRENE is disclosed in accordance with a preferred embodiment of the invention, other materials may be used without departing from the spirit of the present invention.

As with prior hand assisted laparoscopic seal assemblies, the housing 18 of the present seal assembly 10 is secured to the abdominal wall of an individual patient by first creating an incision and positioning the retractor 14 above the incision. Thereafter, the retractor 14, which will eventually be coupled to the seal cap 14, is inserted into the body cavity with the abdominal wall therebetween. The seal cap 12 is then connected to the retractor 14 in a manner securely connecting and supporting the seal cap 12 on the outside of the abdominal wall with the abdominal wall resiliently held between the retractor 14 and the seal cap 12.

More particularly, the surgical site is prepared in accordance with conventional standard hospital procedures, making sure the skin is clean and dry. Thereafter, a template is placed over the incision site and an incision line is marked upon the template using a sterile skin marker. As those skilled in the art will appreciate, the glove size dictates the size of the incision. For example, if the surgeon's glove size is 7, a 6.5 to 7.0 cm incision is usually appropriate. Thereafter, an incision is made along the marked incision line. The incision size is thereafter verified by inserting the surgeon's hand into the abdomen prior to installing the retractor 14 and the present seal cap 10. If the incision is too small, the incision is extended as required on each end to maintain the central position of the incision relative to the placement of the retractor and the present seal assembly 10. Thereafter, the lower retractor ring 22 of the retractor 14 is inserted through the incision. Using one's fingers, the retractor 14 is seated evenly under the peritoneum and the area is swept to ensure the retractor 14 is not lying between tissue layers. In accordance with a preferred embodiment, the upper end 23 of the retractor 14 is secured to the seal cap 12 via an O-ring 24 seated within a recess 25 found in the housing 18, in particular, the lower seal ring 28, of the seal cap 12. As those skilled in the art will certainly appreciate, the retractor may be a fixed length or adjustable length retractor. In either case the retractor 14 must fit the abdominal wall thickness to maintain stability and pneumo. In addition, a removable attachment ring, such as that disclosed in commonly owned U.S. patent application Ser. No. 11/607,118, entitled "Hand Assisted Laparoscopic Device", filed Dec. 1, 2006, is incorporated herein by reference, may be employed within the spirit of the present invention, although those skilled in the art will appreciate other attachment ring structures may be employed without departing from the spirit of the present invention.

In accordance with a preferred embodiment, the iris seal 16 is a rotatable seal which selectively opens under the control of a motor-driven drive assembly 26 to permit passage of a surgeon's hand therethrough and closes under the control of a motor-driven drive assembly 26 in a manner creating a gas tight barrier between the interior abdominal space and the external environment whether or not a hand or instrument is inserted through the seal assembly 10. In particular, the housing 18 in which the iris seal 16 is supported includes a lower seal ring 28 having a track 30 which supports an upper seal ring 32 for relative rotational motion in a manner discussed below in greater detail.

As will be discussed below in greater detail, the upper end 34 of the iris seal 16 is permanently connected to the upper seal ring 32. The lower end 36 of the iris seal 16 is permanently connected to the lower seal ring 28. The upper seal ring 32 and the lower seal ring 28 are connected together for relative rotational movement in a manner allowing for opening and closing of the iris seal 16. In accordance with a preferred embodiment, the upper seal ring 32 and the lower seal ring 28 are connected by at least three snap tabs 38 located on the lower seal ring 28. The snap tabs 38 are shaped and dimensioned to engage a recess 40 along the inner edge 42 of the upper seal ring 32.

An ergonomic cover member 44 is secured to the upper seal ring 32. The ergonomic cover member 44 includes a contoured outer surface 46 providing for improved handling of the upper seal ring 32. In accordance with a preferred embodiment, the ergonomic cover member 44 is a separate component fixedly secured upper seal ring 32 such that rotational force applied to the ergonomic cover member 44 is transmitted on to the upper seal ring 32 for opening and closing of the iris seal 16. However, and as those skilled in the art will certainly appreciate, the ergonomic cover member could be integrally formed with the upper seal ring, while still remaining within the spirit of the present invention.

Figure 7:
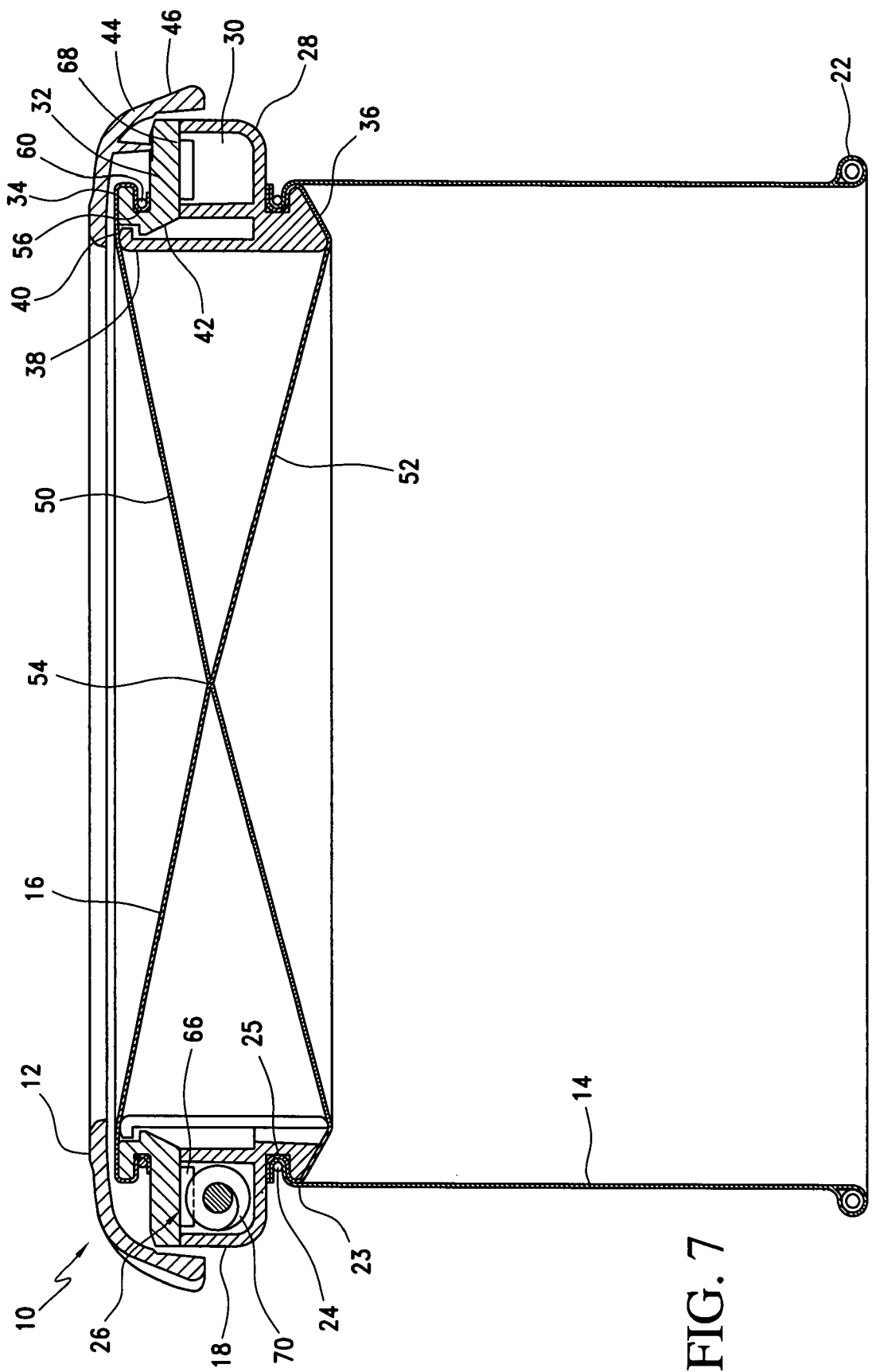
FIG. 7 is a cross sectional view along the line 7-7 in FIG. 5.
Figure 8:
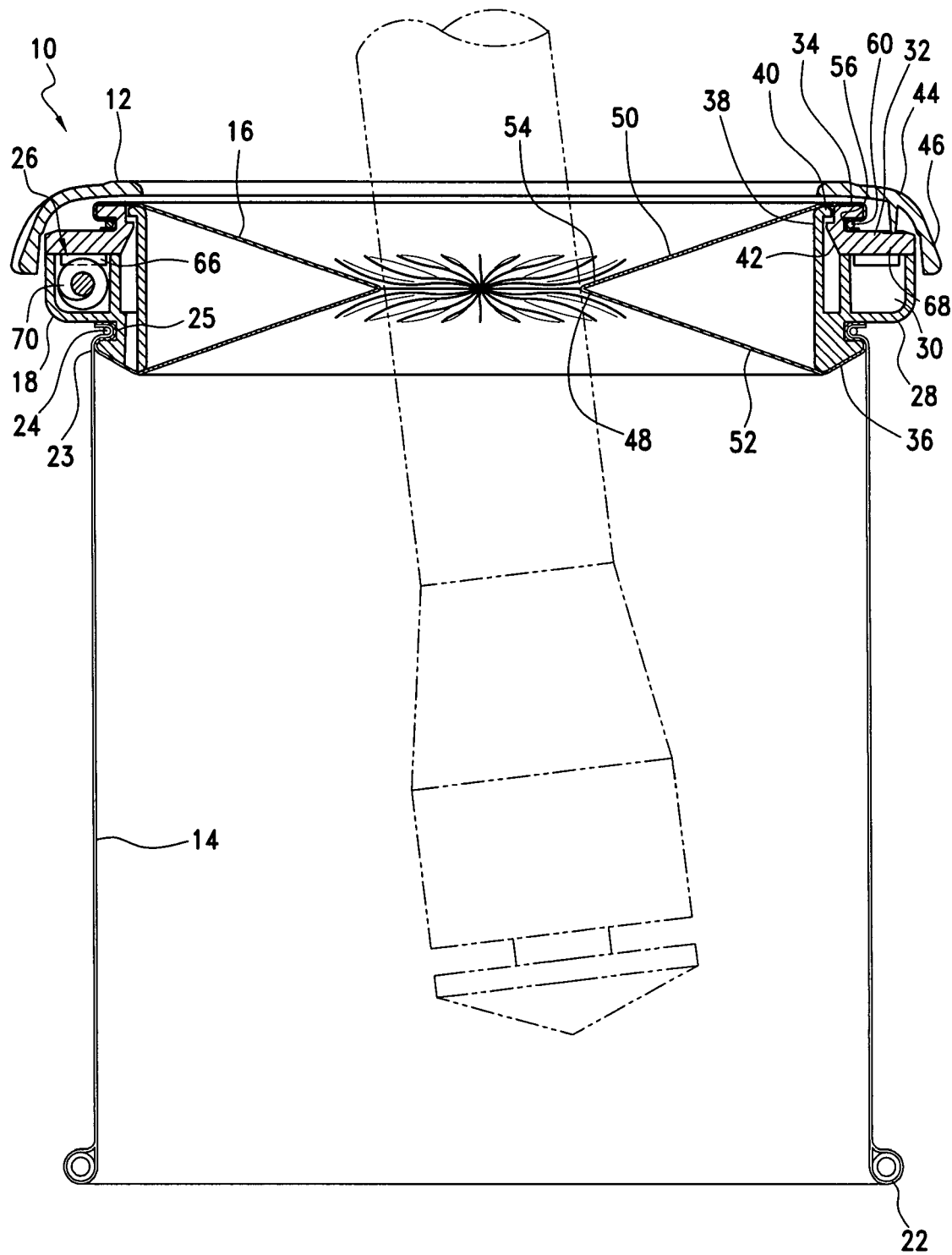
FIG. 8 is a cross sectional view taken along the line 8-8 in FIG. 6 with an instrument shown in phantom.

Referring to FIGS. 3, 7, and 8, the iris seal 16 is shown secured between the upper seal ring 32 and the lower seal ring 28. The upper seal ring 32 is supported within the track 30 of the lower seal ring 28 in a manner facilitating rotational movement between the upper seal ring 32 and the lower seal ring 28. In this way, the rotational movement of the upper seal ring 32 relative to the lower seal ring 28 is utilized to control the opening and closing of the iris seal 16 for insertion of a hand through the present seal assembly 10.

The iris seal 16 is mounted between the upper seal ring 32 and the lower seal ring 28 such that upon rotation of the upper seal ring 32 in a predetermined direction, the central access opening 48 of the iris seal 16 will open providing a surgeon with an access opening for passage of his hand therethrough. Under the control of the motor-driven drive assembly 26 the upper seal ring 32, and ultimately, the iris seal 16 will then rotate in the reverse direction securely closing the access opening 48 about the wrist of the surgeon or instrument. That is, the upper seal ring 32 and the iris seal 16 are moved between an open orientation (see FIGS. 6 and 8) in which an access opening 48 is created within the iris seal 16 and a closed orientation (see FIGS. 5 and 7) in which the iris seal 16 is either wrapped about the wrist of a user with his or her hand inserted therein or substantially fully closed when the iris seal 16 is not in use.

Opening and closing of the iris seal 16 is achieved by constructing the iris seal 16 in a folded configuration spanning the upper seal ring 32 and the lower seal ring 28 in a substantially taut configuration. As such, rotation of the upper seal ring 32 in a first direction will result in an increase of tension along the iris seal 16 in a manner drawing the fold outwardly opening the central access opening 48 in the iris seal 16.

In accordance with the preferred embodiment, the iris seal 16 is composed of a rubber like member. The rubber like member is constructed in the shape of a cylindrical section with the upper and lower sections 50, 52, thereof having a wider diameter than the central section 54 (thereby offering a cross-section as shown in FIGS. 7 and 8). As will be appreciated based upon the following disclosure, the construction of the rubber like member creates a substantially planar iris seal 16 which is closed or opened when the upper seal ring 32 and the lower seal ring 28 are rotated relative to one another in opposite directions.

In accordance with a preferred embodiment, the rubber like member is formed from a thin film having a thickness around less than 0.025 and made from a material having elasticity, such as, natural rubber, synthetic rubber, poly vinyl chloride, silicon and a variety of elastomers (for example, urethane, polyisoprene, silicone). As briefly mentioned above, the rubber like member is cylindrical and includes a central access opening having a predetermined cross sectional area at the central section thereof. The rubber like member is shaped such that the diameter of the opening decreases in the direction from the upper and lower sections to the central section of the rubber like member. Furthermore, the upper and lower ends 34, 36 of the iris seal 16, which are fitted into the grooves 56, 25 of the upper seal ring 32 and the lower seal ring 28 and held therein with o-rings 60, 24 allow for detachment from the upper seal ring 32 and the lower seal ring 28. In accordance with a preferred embodiment, the o-rings 60, 24 are integrated into the iris seal 16, minimizing components and material cost. Because of such detachable structure of the rubber like member, it can be easily replaced by a fresh member when the used rubber like member is broken or worn. This technique would be useful for reusable devices.

Figure 6:
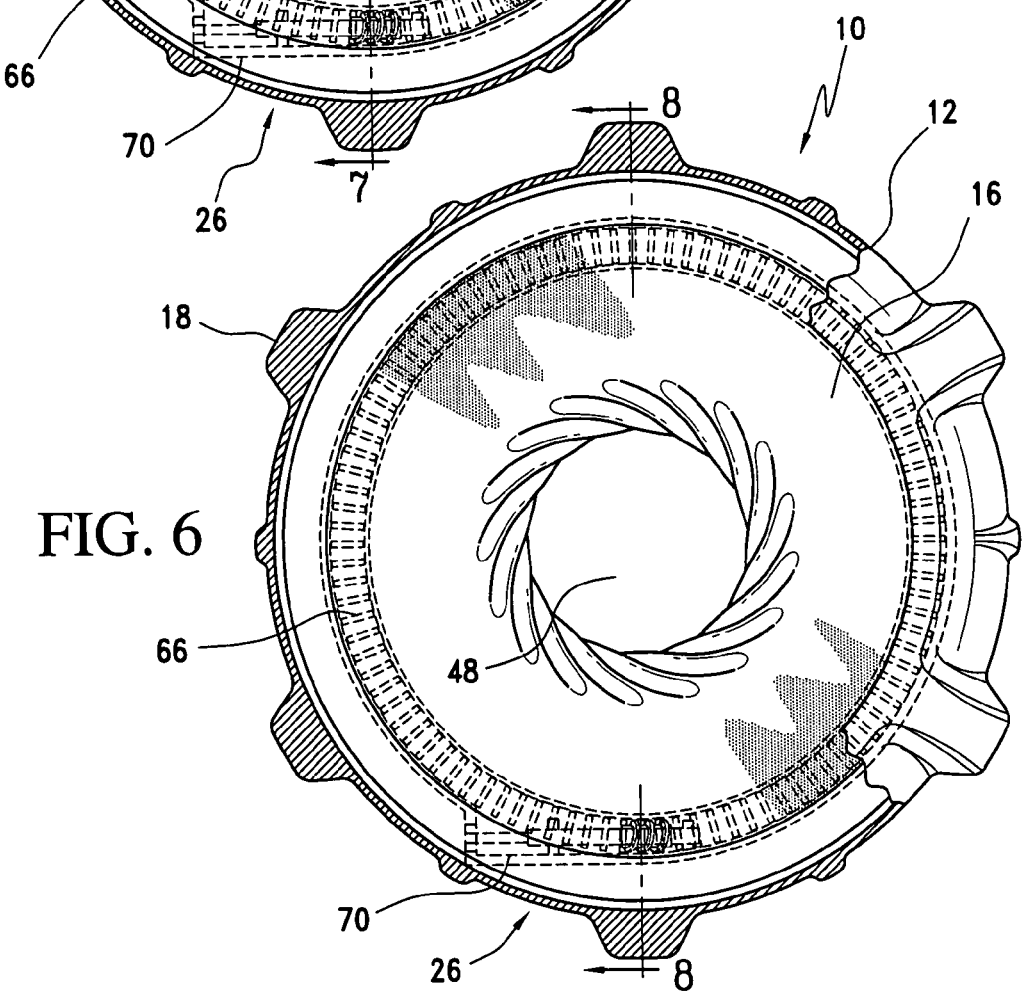

Referring to FIGS. 5, 6, 7 and 8, a plan view and a sectional view are presented, showing the iris seal 16 in its respective closed and open states. FIGS. 6 and 8 show the iris seal 16 in an open state for inserting a member therethrough. This open state is created when the upper seal ring 32 is rotated at a predetermined angle, for example, 15 degrees, from the closed state of the iris seal 16, and the access opening 48 is created. That is, the upper and lower seal rings 32, 28 are rotated relative to each other to facilitate opening and closing of the iris seal 16.

In accordance with a preferred embodiment, the upper seal ring 32 is moved relative to the lower seal ring 28 under the control of a motor-driven drive assembly 26 which is actuated, in accordance with a preferred embodiment, by a hand-held motor assembly 82. By using a hand-held motor assembly 82 with a small motor 64, the iris seal 16 can be opened and closed in a highly controlled manner. The implementation of a hand-held motor assembly 82 in accordance with a preferred embodiment of the present invention, and in the manner discussed below in greater detail, allows a surgeon to easily control the iris seal 16 opening and closing without the assistance of a nurse. In addition, the motor-driven drive assembly 26 eliminates awkward repositioning of the iris seal 16 by eliminating the need to manually interface and rotate the upper and lower seal rings, 32, 28 relative to each other. In practice, and as will be better appreciated based upon the following disclosure, an assistant could readily adjust the iris seal 16 without interfering with the seal assembly 10 or the ongoing procedure. The motor-driven drive assembly 26 also provides for reversible orientation of the upper and lower seal rings 32, 28 and provides for fine adjustment and reusability. This is achieved by the inclusion of forward and reverse bottoms 83a, 83b for controlling rotation of the motor 64.

In accordance with this preferred embodiment, the upper seal ring 32 is provided with a series of gear teeth 66 along its outer perimeter 68, while the lower seal ring 28 is provided with a worm gear 70 shaped, dimensioned and positioned for interacting with the gear teeth 66 of the upper seal ring 32 to cause movement of the upper seal ring 32 relative to the lower seal ring 28. The worm gear 70 includes a first end 72 and a second end 74 supported for rotation by supports 76a, 76b of a recess 86 formed in the lower seal ring 28. The second end 74 of the worm gear 70 is exposed through an external wall 77 of the lower seal ring 28 for selective engagement with a drive cable 78 of the hand-held motor assembly 82. As briefly mentioned above, the worm gear 70 is oriented to interact with the gear teeth 66 formed along the upper seal ring 32 in a manner causing rotation of the upper seal ring 32 relative to the lower seal ring 28.

Actuation of the worm gear 70, and ultimately the upper seal ring 32, is achieved through the provision of an attachment member 80 at the second end 74 of the worm gear 70. The attachment member 80 is shaped and dimensioned to operatively engage a distal end 84 of a drive cable 78 of the hand-held motor assembly 82 for permitting the transmission of rotary motion from the drive cable 78 to the worm gear 70, and ultimately to the upper seal ring 32.

In accordance with a preferred embodiment, the drive cable 78 is part of a simple hand-held motor assembly 82 having a handle 88 for actuation via an operator and a distal, or engagement, end 84 shaped and dimensioned for selective engagement with the attachment member 80 of the worm gear 70. The motor assembly 82 includes the flexible drive cable 78 having the free distal end 84 shaped and dimensioned for selective engagement with the attachment member 80 at the second end 74 of the worm gear 70. As such, when the attachment member 80 at the second end 74 of the worm gear 70 is engaged with the distal end 84 of the drive cable 78, and the motor 64 of the hand-held motor assembly 82 is actuated to rotate the drive cable 78, rotation of the drive cable 78 is transferred to the worm gear 70 which ultimately transfers this rotation to the gear teeth 66 formed along the upper seal ring 32. This causes movement of the upper seal ring 32 relative to the lower seal 28 in a manner opening and/or closing the iris seal 16.

Figure 9:
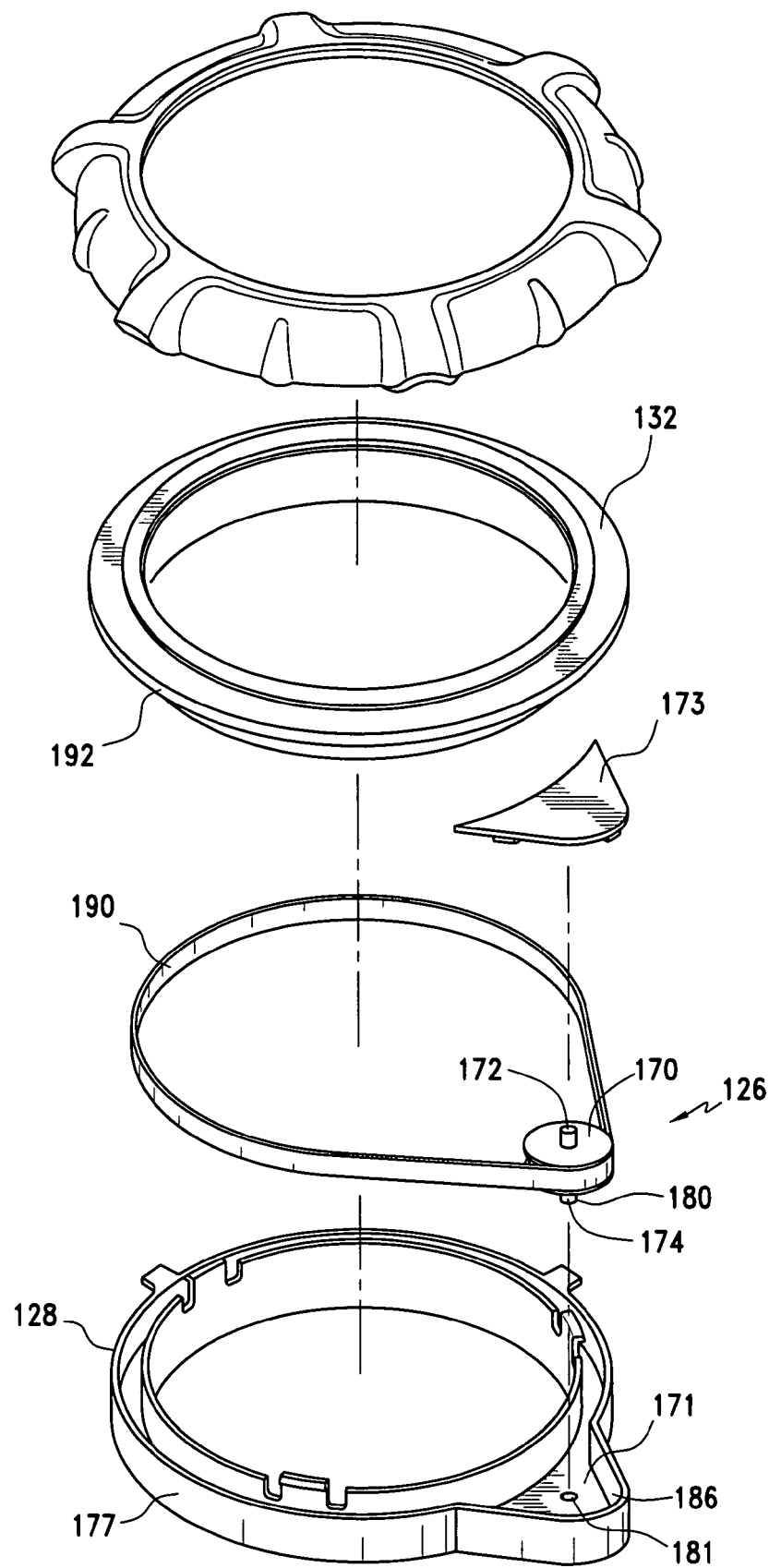
FIGS. 9 and 10 are exploded views showing alternate embodiments of the present hand assisted laparoscopic seal assembly.

In accordance with an alternate embodiment, and as shown with reference to FIG. 9, an alternate motor-driven drive assembly 126 may be employed. In particular, a pinion gear 170 is mounted within a recess 186 formed in the lower seal ring 128. The pinion gear 170 is shaped, dimensioned and positioned for interacting with a drive belt 190 extending around and between the pinion gear 170 of the lower seal ring 128 and an outer circumference surface 192 of the upper seal ring 132 to cause movement of the upper seal ring 132 relative to the lower seal ring 128.

As shown with reference to FIG. 9, the pinion gear 170 is supported within an extended cavity 171 formed in the lower seal ring 128. A cap 173 covers the cavity 171 to protect the pinion gear 170 and other working functional components. The pinion gear 170 includes a first end 172 and a second end 174 pivotally supported by edges of the recess 186 formed in the lower seal ring 128. The pinion gear 170 is oriented within the lower seal ring 128 such that it rotates about an axis which is substantially parallel to the axis about which the upper seal ring 132 rotates. The second end 174 of the pinion gear 170 is exposed through an external wall 177 of the lower seal ring 128 for selective engagement with a drive cable of motor assembly (as disclosed above with reference to FIGS. 1 and 3). As briefly mentioned above, the pinion gear 170 is oriented to interact with the belt 190 in a manner causing rotation of the upper seal ring 132 relative to the lower seal ring 128.

Actuation of the pinion gear 170, and ultimately the upper seal ring 132, is achieved through the provision of an attachment member 180 at the second end 174 of the pinion gear 170 which extends through an aperture 181 in the cavity 173. The attachment member 180 is shaped and dimensioned to operatively engage a distal end of the drive cable for permitting the transmission of rotary motion from the drive cable to the pinion gear 170, and ultimately to the upper seal ring 132. As with the prior embodiment, the drive cable is part of a simple hand-held motor assembly having a handle for actuation via an operator and a distal, or engagement, end shaped and dimensioned for selective engagement with the attachment member 180 of the pinion gear 170. The hand-held motor assembly includes the flexible drive cable having the free distal end shaped and dimensioned for selective engagement with the attachment member 180 at the second end 174 of the pinion gear 170. As such, when the attachment member 180 at the second end 174 of the pinion gear 170 is engaged with the distal end of the drive cable, and the motor of the motor assembly is actuated to rotate the drive cable, rotation of the drive cable is transferred to the pinion gear 170 which ultimately transfers this rotation to the belt 190 encircling the upper seal ring 132. This causes movement of the upper seal ring 132 relative to the lower seal ring 128 in a manner opening and/or closing the iris seal 116.

Figure 10:
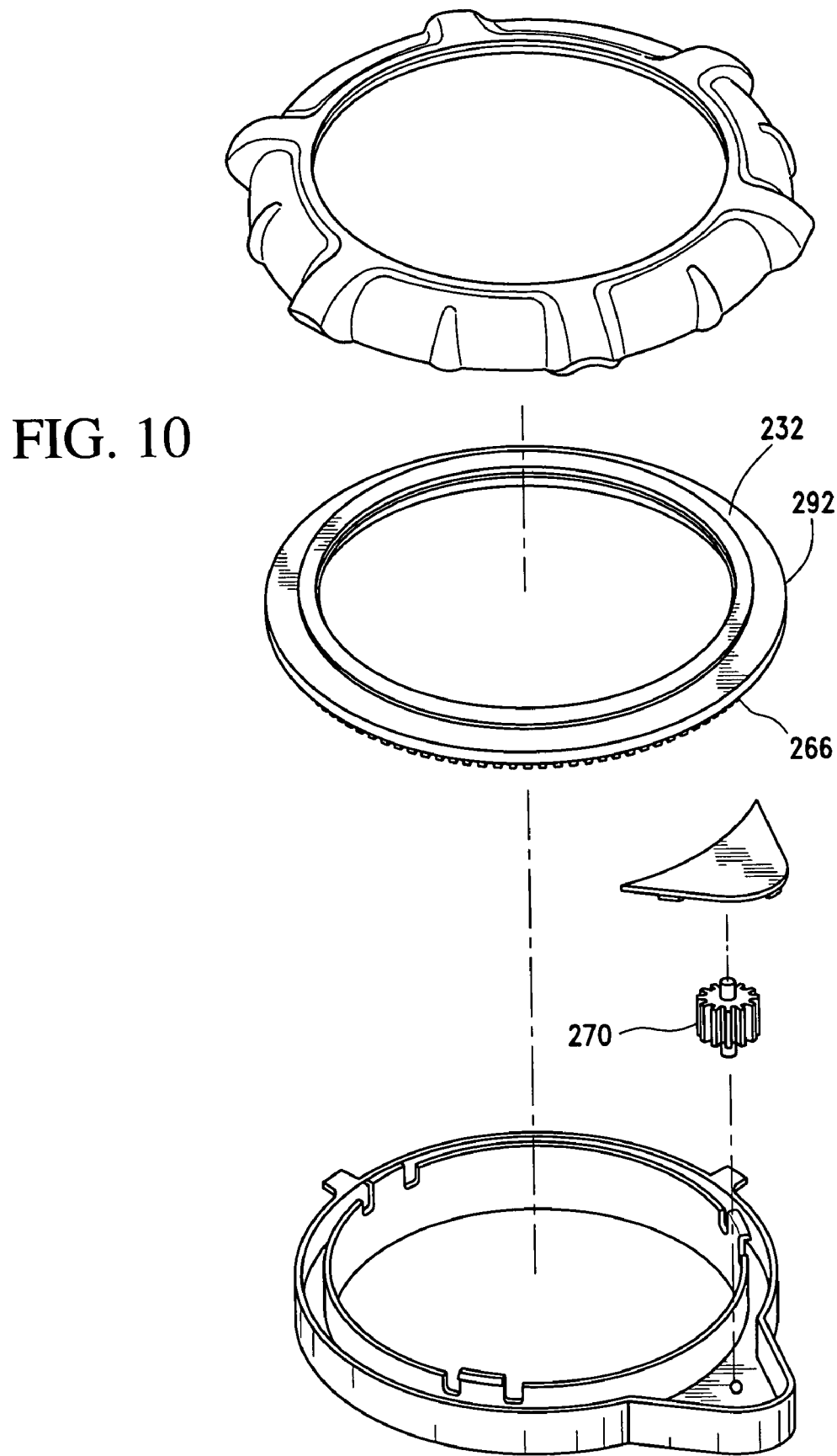

Referring to FIG. 10, an alternate embodiment is disclosed which is similar to that disclosed with reference to FIG. 9. In accordance with this embodiment, a pinion gear 270 could be utilized for engagement with teeth 266 formed along an outwardly facing surface 292 of the upper seal ring 232. Regardless of which of these two embodiments is employed, the pinion gear would be oriented to rotate about an axis substantially parallel to the axis about which the upper seal ring rotates relative to the lower seal ring.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A seal assembly for permitting hand assisted laparoscopic procedures, comprising:
   a seal cap including a seal positioned within a housing, the housing including a lower seal ring having a track which supports an upper seal ring for rotational motion relative thereto, wherein the seal is supported between the upper seal ring and the lower seal ring for rotation between an open orientation and a closed orientation;
   the seal including an upper end connected to the upper seal ring and a lower end connected to the lower seal ring such that relative rotation of the upper seal ring and lower seal ring moves the seal between the open orientation and the closed orientation; and
   a motor-driven drive assembly associated with the lower seal ring and the upper seal ring for controlling relative movement of the upper seal ring and the lower seal ring resulting in opening and closing of the seal.

2. The seal assembly according to claim 1, further including a retractor extending from the seal cap.

3. The seal assembly according to claim 1, wherein the drive assembly includes a worm gear.

4. The seal assembly according to claim 3, further including a hand-held motor assembly adapted for use in conjunction with the drive assembly.

5. The seal assembly according to claim 4, wherein the hand-held motor assembly includes a drive cable that engages the worm gear.

6. The seal assembly according to claim 5, wherein the worm gear engages teeth formed along the upper seal ring.

7. The seal assembly according to claim 1, wherein the drive assembly includes a pinion gear.

8. The seal assembly according to claim 7, wherein the pinion gear engages a belt encircling the upper seal ring.

9. The seal assembly according to claim 7, wherein the pinion gear engages teeth formed along the upper seal ring.

10. The seal assembly according to claim 7, further including a hand-held motor assembly adapted for use in conjunction with the drive assembly.

11. The seal assembly according to claim 10, wherein the hand-held motor assembly includes a drive cable that engages the pinion gear.

12. The seal assembly according to claim 1, wherein the seal in an iris seal.

13. The seal assembly according to claim 1, further including a hand-held motor assembly adapted for use in conjunction with the motor-driven drive assembly.

14. The seal assembly according to claim 13, wherein the hand-held motor assembly includes a drive cable.

15. The seal assembly according to claim 12, wherein the seal is composed of a rubber like member.

16. The seal assembly according to claim 12, wherein the seal is constructed in the shape of a cylindrical section with upper and lower sections and a central section therebetween.

* * * * *